US010849852B2

(12) United States Patent
McGarrah et al.

(10) Patent No.: US 10,849,852 B2
(45) Date of Patent: Dec. 1, 2020

(54) PET FOOD INCLUDING CANNABIDIOLIC ACID (71) Applicants: Steven M. McGarrah, Kansas City, MO (US); Thomas A. Asquith, Cincinnati, OH (US)

(72) Inventors: Steven M. McGarrah, Kansas City, MO (US); Thomas A. Asquith, Cincinnati, OH (US)

(73) Assignee: High Plains Nutrition, LLC, Ferrelview, MO (US)

( * ) Notice: Subject to any disclaimer, the term of this patent is extended or adjusted under 35 U.S.C. 154(b) by 286 days.

(21) Appl. No.: 15/923,695

(22) Filed: Mar. 16, 2018

(65) Prior Publication Data

US 2019/0091144 A1 Mar. 28, 2019

Related U.S. Application Data (60) Provisional application No. 62/473,369, filed on Mar. 18, 2017.

(51) Int. Cl.
| | |
|---|---|
| *A61K 9/00* | (2006.01) |
| *A23K 20/158* | (2016.01) |
| *A23K 10/30* | (2016.01) |
| *A23K 10/00* | (2016.01) |
| *A23K 30/00* | (2016.01) |
| *A23K 40/25* | (2016.01) |
| *A23K 50/42* | (2016.01) |
| *A23K 20/111* | (2016.01) |
| *A61K 31/047* | (2006.01) |
| *A61K 31/192* | (2006.01) |
| *A61K 31/352* | (2006.01) |
| *A61K 36/185* | (2006.01) |
| *A23K 50/75* | (2016.01) |
| *A23L 25/00* | (2016.01) |
| *A23L 33/12* | (2016.01) |
| *A23L 27/60* | (2016.01) |
| *A23L 33/105* | (2016.01) |
| *A23L 13/40* | (2016.01) |
| *A23D 7/005* | (2006.01) |
| *A23G 3/40* | (2006.01) |
| *A23G 3/48* | (2006.01) |
| *A23G 4/06* | (2006.01) |
| *A23G 9/32* | (2006.01) |
| *A23G 9/42* | (2006.01) |

(52) U.S. Cl.
CPC ............ *A61K 9/0056* (2013.01); *A23K 10/00* (2016.05); *A23K 10/30* (2016.05); *A23K 20/111* (2016.05); *A23K 20/158* (2016.05); *A23K 30/00* (2016.05); *A23K 40/25* (2016.05); *A23K 50/42* (2016.05); *A61K 31/047* (2013.01); *A61K 31/192* (2013.01); *A61K 31/352* (2013.01); *A61K 36/185* (2013.01); *A23D 7/0056* (2013.01); *A23G 3/40* (2013.01); *A23G 3/48* (2013.01); *A23G 4/066* (2013.01); *A23G 4/068* (2013.01); *A23G 9/327* (2013.01); *A23G 9/42* (2013.01); *A23K 50/75* (2016.05); *A23L 13/43* (2016.08); *A23L 25/30* (2016.08); *A23L 27/60* (2016.08); *A23L 33/105* (2016.08); *A23L 33/12* (2016.08); *A23V 2002/00* (2013.01)

(58) Field of Classification Search
CPC ...... A61K 9/00; A61K 36/185; A61K 31/047; A61K 31/352; A23K 20/158; A23K 20/111; A23K 30/00; A23K 50/42; A23K 40/25
See application file for complete search history.

(56) References Cited

U.S. PATENT DOCUMENTS

2005/0112259 A1  5/2005  Fernando

FOREIGN PATENT DOCUMENTS

WO  PCT/US 18/22985  3/2018

OTHER PUBLICATIONS

Da Porta et al. Fatty acid composition and oxidation stability of hemp (*Cannabis sativa L.* ) seed oil extracted by supercritical carbon dioxide Feb. 2012. Industrial Crops and Products 36(1):401-404 V W X.*
Parry et al. "Radical Scavenging Properties of Cold-Pressed Edible Seed Oils", Jul. 21 ,2005, Phenolic Compounds in Foods and Natural Health Products, pp. 107-117, p. 1, Para (1).
Callaway et al. "Hempseed Oil" Apr. 2009 Gourmet and Health Promoting Specialty Oils, Chapter 6, pp. 185-213, pp. 1-36, p. 6 Full Para (1).

(Continued)

*Primary Examiner* — Shirley V Gembeh
(74) *Attorney, Agent, or Firm* — Hoban Law Group; Kevin H. Fortin (57) ABSTRACT

A pet food product includes a food substrate manufactured by extrusion, baking or other process involving heat. The pet food product includes less than 10% of hemp oil by weight, and preferably less than 5% by weight. The hemp oil has cannabinoids, including acidiccannabinoids. The acidic cannabinoids have a concentration of less than 100 parts per million, and preferably between 10-40 parts per million in the hemp oil. The acidic cannabinoids include cannabidiolic acid (CBD-A) and cannabidiol (CBD) in a ratio of at least 1:1, and preferably 3:1, or greater. An antioxidant is added to the hemp oil to inhibit oxidation of the acidiccannabinoids including the (CBD-A). The pet food product includes a second oil blended with the hemp oil. The antioxidant and the second oil cooperate to inhibit oxidation of the acidic cannabinoids.

3 Claims, 2 Drawing Sheets (56) References Cited

OTHER PUBLICATIONS

PCT Search Report received in PCT/US18/229895 dated Aug. 23, 2018,. pp. 3.
Manufacturers Hemp Seed Oil Nutritional Description.
Hindawin Publishing Corporation Parkinson's Disease Marijuana Compounds: A Non conventional Approach Parkinson's Disease Therapy Mariana Babayeva, Haregewein Assefa, Paramita Basu, Sanjeda Chumki, and Zvi Loewy New York 2016.
Toxicology Brief Marijuana Exposure in Animals Caroline W. Donaldson.
Epilepsy & Behavior The Legal Status of Cannabis and Cannabidoil under U.S Law Alice Mead 2008.
Science Direct Journal of Pharmaceutical and Bomedical Analysis A rapid and simple procedure for the determination of cannabinoids in hemp food products by gas chromatography mass spectrometry Manuela Pellegrini, Emilia Marchei, Roberta Pacific!, and Simona Pichini.
PLOS ONE Mice expressing a hyper sensitive form of the CB1 Cannabinoid receptor CB1 show modestly enhanced alcohol preference and consumption David Marcus, Angela Henderson-Redmond, Maciej Gonek, Michael Zee, Jill Farnshworth, Ranada Amin, Mary Jeanette Andrews, Brian Davis, Ken Mackie, and Daniel Morgan.
Scientific Reports 2015 Mitochondrial ADP/ATP exchange inhibition: a novel off target mechanism underlying ibipinabant induced myotoxicity Tom Schirris, Tina Ritschel, Herma Renkema, Peter Willems, Jan Smeitink, and Frans Russel.
New Cannabinoid-Like Chromane and Chromene Derivations from Rhododendron anthopogonoides Naoki Iwata and Susumu Kitnaka Chiba, Japan 2011.
Xenobiotica Non-clinical evaluation of the metabolism, pharmacokinetics, and exertion of S-777469, a new cannabinoid receptor 2 selective agonist Kazutaka Sekiguchi, Takushi Kanazu, Masajaru Takeuchi, Hiroshi Hasegwa and Yoshitaka Yamaguchi.
Elsevier Pharmacokinetic and behavioral profile of THC, CBD, and THC +CBD combination after pulmonary, oral, and subcutaneous administration in rats and confirmation of conversion in vivo of CBD to THC Tomas Hlozek, Libor Uttl, Lukas Kaderabek, Marie Balikova, Eva Lhotkova, Kristyna Stefkova, Filip Tyls, Martin Kuchar, and Tomas Palenicek.
Pharmacological and Therapeutic Secrets of Plant and Brain (Endo) Cannabonoids Lumirondrej Hanus Department of Medicinal Chemistry and Natural Products 2008.
Substance Abuse and Rehabilitation The Cannabis withdrawl syndrome:current insights Udo Bonnet Ulrich W. Preuss 2017.
The Composition of Hemp Seed Oil and Its Potential as an Important Source of Nutrition Cary Leizer, David Ribnicky, Alexander Poulev, Slavik Dushenkov, and Ilya Raskin.
The decomposition of acidic and neutral cannabinoids in organic solvents R.N. Smith and C.G Vaughan London 1977.
British Journal of Pharmacology The dual neuroprotective-neurotoxic profile of cannbinoid drugs Yosef Sarne, Fadi Asaf, Miriam Fishbein, and Ora Keren.
The endocannabinoid system in normal and pathological brain ageing Andras Bilkei-Gorzo Germany.
BMC Pharmacology and Toxicology The grass isn't always greener: The effects of cannabis on embryological development Joseph Friedrich, Dara Khatib, Keon Parasa, Ariana Santopetro and G. Ian Gallicano.
The Influence of Long-term Storage Conditions on the Stability of Cannabinoids derived from Cannabis Resin Irenne Gabriela Trofin, Gariel Dabija,, Danut-Ionel Vaireanu, and Laureniu Filpenscu.
Scidence Direct European Journal of Pharmacology The non-psychoactive cannabis constituent cannabidiol is an orally effective therapeutic agent in rat chronic inflammatory and neuropathic pain Barbra Costa, Anna Elisa Trovato, Francesca Comelli, Gabriella Giagnoni, and Maraiapia.
How Accurate is Potency Testing 2011 Dale Gieringer and Arno Hazenkamp.
Eyphytica Time course of cannabinoid accumulation and chemotype development during the growth of Cannabis sativa L D. Pacifico, F.Miselli, A. Carboni, A. Moschella, and G. Mandolino.
J. Neuroimmune Pharmacol Turning over a new leaf, cannabinoid and endocannabinoid modulation of immune function Guy A. Cabral, Thomas J. Rogers, and Aron H. Lchtman.
The Journal of Biological Chemistry Type 1 Cannabinoid Receptor Ligands Display Functional Selectivity in Cell Culture Model of Striatal Medium Spiny Projection Neurons Robert Laprairie, Amina Bagher, Melanie Kelly, Denis Durpre, and Eileen Denovan-Wrght.
Open Access Understanding Cannabinoid Psychoactive with Mouse Genetic Models Ken Mackie.
UNODC Recent advances in the chemical research of cannabis Ljubi Grlic.
ANZFA Final Assessment Report Use of industrial hemp as a novel food.
7orensic Toxicol 2007 Conversion of cannabidiol to 9-tetrahydrocannabinal and related Cannabinoid in artificial gastric juice, and their pharmacological effects in mice Yuka Itokawa, Satoshi Yamaori, Tatsuya Funahahi, Toshiyuki Kaji, and Ikuo Yamamoto.
Cannabidiol: from an inactive cannabiniod to a drug with wide spectrum of action Antonio Waldo Zuardi.
Hemp Seed (Cannabis sativa L.) Proteins: Composition, Structure, Enzymatic Modification, and Functional or Bioactive Properties R.E. ALUKO University of Manitoba, Winnipeg, MB, Canada.
Journal of Agricurtural and Food Chemistry Hemp (Cannabis sativa L.) Seed Oil: Analytical and Phytochemical Characterization of the Unsaponifiable Fraction S. Montserrat-De Law Paz, F. Marin-Aguilar, M.D Garcia-Gimenez, and M.A. Fernadez-Arche. Department of Pharmacology, Faculty of Pharmacy, University of Seville, 41012 Seville, Spain ‡Laboratory of Cellular and Molecular Nutrition, Instituto de la Grasa, Spanish National Research Council (CSIC), 41012 Seville, Spain.
Hemp seed oil: A source of valuable essential fatty acids Jean Luc, and David W. Pate International College of Hospitality Administration, Englisch Gruss Strasse 43, CH3900 Brig, Switzerland . 2 HortaPharm B.V., Schinkelhavenkade 6.
Hempseed Oil J.C Allaway and David W. Pate 2010 (36 Pages) Kuopio, Finland.
O'Shaughnessy's 2011 (2Pages) How Accurate is Potency Testing? Dale Gieringer and Arno Hazenkamp.
Cannabis and Cannabinoid Research 2017 Identification of a Widespread Palmitoylethanolamide Contamination in Standard Laboratory Glassware Roberto Angelini, Donovan A. Argueta, Daniel Piomelli, and Nicholas V. Diparrizio.
Cannabis and Cannabinoid Research 2016 Identification of Psychoactive Degradants of Cannabidiol in Simulated Gastric and Physiological Fluid John Merrick, Brian Lane, Terri Sebree, Tony Yakah, Carol O'Neill, and Stan L. Banks.
[NIH Public Access 2009] In vivo pharmacology of endocannabinoids and their metabolic inhibitors. Therapeutic implications in Parkinson's disease and abuse liability Andread Giuffrida and Lance R. McMahon Department of Pharmacology, University of Texas Health and Science Center, San Antonio, TX.
British Journal of Pharmacology Inhibitory effect of cannabichromene, a major non-psychotropic cannabinoid extract from Cannabis sativa, on inflammation-induced hypermotility in mice Angelo A Izzo, Raffaele Capasso, Gabriella Aviello, Francesca Borrelli, Barbara Romano, Fabian Piscitelli, Laura Gallo, Francesco Capasso, Pierangelo Orlando, and Vincenzo Di Marzo.
Frontiers in Pharmacology 2017 Involvement of Cannabinoid Signaling in Vincristine-Induced Gastrointestinal Dysmotility in the Rat Gema Vera, Ana E. Lopez-Perez, Jose A, Uranga, Rocio Giron, Isabel Martin=Fontelles, and Raquel Abalo.
Liquid Chromatography Time of Flight Mass Spectrometry for Cannabinoid Profiling and Quantization in Hemp Oil Extracts Anthony Macherone, Joan Stevens, Mike Adams, A. Roth, Karen Kiakaris, Sue D'Antonio and Rita Steed.
British Journal of Pharmacology 2010 Themed Issue: Cannabinoids Phytocannabinoids beyond the Cannabis plant—do they exist? Jurg Gertsch, Roger Pertwee and Vincenzo Di Marzo Bern, Switzerland.

(56) References Cited

OTHER PUBLICATIONS

Natural Product Reports 2016 Phytocannabinoids: a unified critical inventory Lumir Ondrej Hanus, Stefan Martin Meyer, Eduardo Munoz, Orazio Taglialatela Scafati, and Giovanni Appendiono.
British Journal of Pharmacology 2005 Plant cannabinoids: a neglected pharmacological treasure trove Raphael Mechoulam Department of Medicinal Chemistry and Natural Products Jerusalem Israel.
Cannabis and Cannabinoid Research Prevalence and Correlates of Cannabis Use in Outpatients with Serious Mental Illness Receiving Treatment for Alcohol Use Disorders Jordan Skalisky, Emily Leickly, Oladunni Oluwoye, Sterling McPherson, Debra Srebnik, John Roll, Richard Ries, and Michael McDonell.
HHS Public Access Prior stimulation of the endocannabinoid system prevents methamphetamine-induced dopaminergic neurotoxicity in the striatum through activation of CB2 receptors Joelle Nader, Cinzia Raping, Benjamin Gennequin, Francois Chavant, Maureen Fracheteau, Alexandros Makiyannis, Andrea Duranti, Mauro Maccarrone, Marcello Solinas and Nathalie Thiriet.
UNODC Recommended methods for the identification and analysis of cannabis and cannabis products.
Role of Cannabinoids in Pain Management Than B. Russo and Adnrea G. Hohmann.
HHS Public Access Role of Endocannabinoid Activation of Peripheral CB1 Receptors in Regulation of Autoimmune Disease Jessica Margaret Sido, Pakash S. Nagarkatti, and Mitzo Nagarkatti.
Role of Endocannabinoids and Cannabinoid-1 Receptors in Cerebrocortical Blood Flow Regulation Andras Iring, Eva Ruisanchez, Bela Horvath, Rita Benko, Zsombor Lacza, Zoltan Jarai, Peter Sandor, Vincenzo Di Marzo, Pal Pacher, and Zoltan Benyo.
Current Drug Safety 2011 Safety and Side Effects of Cannabidiol, a *Cannabis sativa* Constituent Mateus Machado Bergamaschi, Regina Helena Costa Queroz, Jose Alexandre S. Crippa, and Antonio Waldo Zuardi.
Safety and Toxicology of Cannabinoids Jane Sachs, Erin McGlade, and Deborah Yurgelun-Todd.
Secondary metabolism in cannabis Phyotchem Rev 2008 Isvett Josefina Flores-Sanchez and Robert Verpoorte.
PLOS ONE Spatial distribution of cannabinoid receptor type 1 in normal canine central peripheral nervous system 22 pages Jessica Freundt-Revilla, Kristel Kegler, Wolfgang Baumgartner, and Andrea Topold.
Occurrence of omega-3 stearidonic acid (cis-6,9,12,15-octadecatetraenoic acid) in hemp (*Cannabis sativa* L.) seed J.C Callaway T. Tennila and D.W. Pate Department of Pharmaceutical Chemistry 4 pages.
CrossMark Synhesis, characterization and degration behavior of thermoplatic polyurethane from hydroxylated hemp seed oil Rajendran Surender, Arunjunai Raj Mahendram, Gunter Wuzella, and Chinnaswamy Thangavel Vijajkumar.
British Journal of Pharmacology Taming THC:potential cannabis synergy and phytocannabinoid-terpenoid entourage effects Ethan B. Russo.
Plant Biotechnology Journal 2014 Targeted mutation of 12 and 15 desaturase genes in hemp produce major alterations in seed fatty acid composition including a high oleic hemp oil Monika Bielecka, Filip Kaminski, Ian Adams, Helen Poulsn, Raymond Sloan, Yi Li, Tony Larson, and Ian Graham.
Drug Development and Industrial Pharmacy Temperature Stability and Bioadhesive Properties of 9-tetrahydrocannabinol Incorporated Hyroxypropylcellulose Polymer Matrix Systems 13 pages Michael A. Repka and Mahmoud A. Elsohly.
THC and Cannabinoid Testing J.C Callaway 23rd Annual Conference of the HIA 2016.
British Journal of Pharmacology The anit-inflammatory mediator palmitoylethanolamide enhances the levels of 2-arachidonoyl-glycerol and potentiates its actions at TRPV1 cation channels Stefania Petrosino, Anillo Schiano Moriello, Santiago Cerrato, Mariella Fusco, Anna Puigdemont, Luciano De Petrocellis and Vincenzo Do Marzo.
The Biosynthesis of Cannabinoids F. Degenhardt, F. Stehle, and O. Kayser Laboratory of Technical Biochemistry, Department of Biochemical and Chemical Engineering 11 pages.
HHS Public Access the Cannabinoid Acids, Analogs and Endogenous Counterparts Sumner H. Burstein Department of Biochemistry and Molecular Pharmacology.
True Farma, Treatibles CBD-Rich Oil Drops for Pets (4 Pages).
Acssymposium Series, John W, Parry, Kequan Zhou, and Lingli Yu, Radical Scavenging Properties of Cold-Pressed Edible Seed Oils. (2 Pages).
Hempseed Oil, J.C. Callaway, PhD and David W. Pate, PhD, 2008-2009 (34 Pages).
What is the Degardtion/Oxidation Pathway of THC When Stored in Air, 2016 (3 Pages).
Fatty Acid Composition and Oxidation Stability of Hemp, Mar. 2012 (6 Pages).
National Composition of Hemp Seed and Oil (1 Page).
Daintri—CBD vs. CBDA:What's the Difference? Oct. 25, 2017 (8 Pages).
What Hemp CBD Can Do for Your Dog or Cat (6 Pages).
9 Plants That Contain Therapeutic Cannabinoids, Allie Beckett, May 16, 2017.
A Chemotaxonomic Approach to the Fatty Acid and Tocochromanol Content of *Cannabis sativa*, Eyup Bagci, Ludger Bruehs, Kurt Aitzetmuller, Yasin Altan, Sep. 27, 2002.
A Conversion of Oral Cannabidiol T Delta9-Tetrahydrocannabinal Seems Not to Occur in Humans, Gerhard Nahler, Franjo Groternhermen, Antonio Waldo, Jose A.S.Crippa 2017 (6 Pages).
A Historical Overview of Chemical Research on Cannabinoids, Raphael Mechoulam, Lumir Hanus, June 2000. (13 Pages).
A Systematic Review and Meta-Analysis of the Haemodynamic Effects of Cannabidiol (13 Pages).
Care and Feeding of the Endocannabinoid System: A Systematic Review of Potential Clinical Interventions that Upregulate the Endocannabinoid System John M. McPartland, Geoffrey W. Guy, Vincenzo Di Marzo.
Therapeautic Potential of Acidic Cannabinoids and Cannabis Entourage Effect, Dr. Jokubas Ziburkus, PHD 2016.
Affinity and Efficacy Studies of Tetrahydrocannabinolic Acid A at Cannabinoid Receptor Types One and Two John M. McPartland, Christa Macdonald, Michelle Young, Phillip S. Grant, Daniel P. Furkert, and Michelle Glass (9 Pages).
Alterations of endocannabinoids in cerebrospinal fluid of dogs with epileptic seizure disorder Felix K. Gesell Alexander A. Zoerner Christina Brauer 2013.
Hempseed as a nutritional resource: An overview J.C. Callaway (2004).
An Update on Safety and Side Effects of Cannabidiol: A Review of Clinical Data and Relevant Studies Kerstin Iffland and Franjo Groternhermen 2017.
Analysis of cannabinoids in commercial hemp seed oil and decarboxylation kinetics studies of cannabidiolic acid (CBDA) Authors: Cinzia Citti, Barbara Pacchetti, and Maria 2017.
Analytical Characterization of Hempseed (Seed of *Cannabis sativa* L.) Oil from Eight Regions in China Tianpeng Chen; Jinfeng He; Jianchun Zhang; Hua Zhang; Ping Qian; Jianxiong Hao; Lite Lit.
Animal Models of Beryllium-induced Lung Disease, Gregory L. Finch, Mark D. Hoover, Fletcher F. Hahn, Kristen J. Nikula, Steven A. Belinsky, Patrick J. Haley, and William C. Griffith Inhalation Toxicology Research Institute, Albuquerque, New Mexico, 1996.
Anticancer mechanisms of cannabinoids G. Velasco, C. Sanchez and M. Guzman 2016.
Aryl Piperazinyl Ureas as Inhibitors of Fatty Acid Amide Hydrolase, (FAAH) in Rat, Dog, and Primate John M. Keith, Rich Apodaca, Mark Tichenor, Wei Xiao, William Jones, Joan Pierce, Mar Seierstad, James Palmer, Michael Webb, Mark Karbarz, Brain Scott, Sandy Wilson, Lin Luo, Michelle Wennerholm, Leon Chang, Sean Brown, Michele Rizzolo, Raymond Rynberg, Sandra Chaplan, and J. Guy Breitenbucher.
Assessment of the relationship between body weight and gastrointestinal transit times measured by use of a wireless motility capsule system in dogs. Carlo S. Boillat, Dr. Med Vet, Frederic P. Gaschen, Dr. Habil, Giselle L. Hosgood.

(56) References Cited

OTHER PUBLICATIONS

Assessment of the Variation Associated with Repeated Measurement of Gastrointestinal Transit Times and Assessment of the Effect of Oral Ranitidine on Gastrointestinal Transit Times Using aWirelessMotility Capsule System in Dogs Jonathan A. Lidbury,1 Jan S. Suchodolski,1 Renata Ivanek,2 and J''orgM. Steiner1.
Association of Expanded Disability Status Scale and Cytokines after Intervention with Co-supplemented Hemp Seed, Evening Primrose Oils and Hot-natured Diet in Multiple Sclerosis Patients Sohelia Rezapour-Firouzi, Seyed Rafie Arefhosseini, Mehdi Farhoudi, Mehrangiz Ebrahimi-Mamghi, Mohamman-Reza Rashidi, Mohammad-Ali Torbati, Behzad Baradaran.
Beta-caryophyllene is a dietary cannabinoid Ju Rg Gertsch, Marco Leonti, Stefan Raduner, Illdiko Racz, Jian-Zong Chen, Xiang-Qun Xie, Karl-Heinz Altman, Meliha Karsak, and Andreas Zimmer.
Bioactive Carbohydrates and Peptides in Foods: An Overview of Sources, Downstream Processing Steps and Associated Bioactivities Maria Hayes and Brijesh K. Tiwari.
Bioactivities of alternative protein sources and their potential health benefits A. Philanto, P. Mattila S. Makinena and M. Pajari.
Blood levels do not predict behavioral or physiological effects of Δ9-tetrahydrocannabinol in rhesus monkeys with different patterns of exposure. Brett C. Ginsburg, Lenka Hurba, Armia Zaki, Martin Javors, and Lance R. McMahon.
British Medical Journal (1917).
Canine Cutaneous Plasmacytosis: 21 Cases (2005-2015) B.O. Boostorm, A.S. Moore, C.J. Deregis, C. Robat, K. Freeman, and D.H. Thamm.
Phytocannabinoids and Cannabis Terpenoids Ethan Russo.
Cannabidiol: Pharmacology and potential therapeutic role in epilepsy and other neuropsychiatric disorders. Orrin Devinsky, Maria Roberta Cilio, Helen Cross, Javier Fernandez-Ruiz, Jacqueline French, Charlotte Hill, Russel Katz, Vincenzo Do Marzo, Didier Jutras-Asward, William George Notcutt, Jose Martinez-Orgado, Philip J Robson, Brian G. Rohback, Elizabeth Thiele, Benjamin Whalley, and Daniel Friedman.
Cannabidiol, a non-psychotropic plant-derived cannabinoid, decreases inflammation in a murine model of acute lung injury: Role for the adenosine A2A receptor. Alsion Ribeiro, Viviane Ferraz-De-Paula, Milena L. Pinheriro, Luna B. Vitoretti, Domenica P. Mariano-Souzs, Wanderely M. Quniteriro-Filho, Adriano T. Akamine,Vinicius I. Alemida, Joao Quevedo, Felipe Dal-Pizzol, Jamie E. Hallak, Antonio W. Zuardi, Jose A. Crippa, AD Joao Palermo-Neto 2012.
Cannabinoid Chemistry, Lumir Hanus, Raphael Machoulam, 2005.
Cannabinoid pharmacology: the first 66 years Roger G. Pertwee 2006.
Cannabinoid Receptor Antagonist-Induced Striated Muscle Toxicity and Ethylmalonic-Adipic Aciduria in Beagle Dogs. Lindsay Tomlinson. Mark Tirmenstein, Evan Janovitz, Nelly Aranibar, Karl-Heinz Ott, John Kozolosky, Laura Patrone, William Achanzar, Karen Augustine, Kimberly Brannen, Kenneth Carlson, Jeffery Charlap, Katherine Dubrow, Liya Kang, Laura Rosini, Julieta Panzica-Kelly, Oliver Flint, Frederic Moulin, John Megill, Haiying Zhang, Michael Bennett & JosephHorvath.
Cannabinoid-Induced Hyperemesis: A Conundrum—From Clinical Recognition to Basic Science Mechanisms Nissar A. Darmani.
Cannabinoids in health and disease Natalya M. Kogan, Raphawl Mechoulam 2007.
Halent Laboratories, Cannabinoids Primer.
Cannabinoids: Potential Anticancer Agents Manuel Guzamn 2003.
Health Canada—Cannabis Information for Healthcare 2013.
Cannabis and endocannabinoid modulators: Therapeutic promises and challenges Igor Granta and Rael Cahnb 2005.
Frontiers in Plan Science: *Cannabis sativa*: The Plant of the Thousand and One Molecules Christelle M. Andre, Jean-Francios Hausaman and Gea Guerriero 2016.
American Physiological Society CB1R antagonist increases hepatic insulin clearance in fat-fed dogs likely via upregulation of liver adiponectin receptors 2015 (12 pages) Morvarid Kabir, Malini S. Iyer, Joyce M. Richey. Orison O. Woolcott, Isaac Asare Bediako,
Qiang Wu, Stella P. Kim, Darko Tefanovski, Cathryn M. Kolka, Isabel R. Hua, Karyn J. Catalano, Jenny D. Chiu, Viorica Ionut, and Richard N. Bergman.
The American Society for Pharmacology and Experimental Therapeutics CB2 Cannabinoid Receptors as a Therapeutic Target—What Does the Future Hold? Amey Dhposehwarker and Ken Mackie Bloominton, Indiana 2014.
Journal of Analytical Toxicology Delta9-tetrahydrocannabinol Content of Commercially Available Hemp Products Justin M. Holler, Thomas Z. Bosy, Christopher S. Dunkley, Barry Levine, Marilyn R. Pastm and Aaron Jacobs, Jul.-Aug. 2008; 32(6):428-32.
Medical Chemistry CB2-Selective Cannabinoid Receptor Ligands: Synthesis, Pharmacological Evaluation, and Molecular Modeling Investigation of 1,8-Naphthyridin-2(1H)-one-3-carboxamides 2014 (15 Pages) Valentina Luccesi, Dow P. Hurst, Derek M. Shore, Simone Bertini, Brandie Ehrmann, Marco, Allara, Lyle Lawrence, Macchia, Vincenzo Di Marzo, Mary E. Abood, Patricia H. Reggio, and Clementina Manera.
British Pharmacological Society 2013 (19 pages) Characterization of cannabinoid receptor ligands in tissues natively expressing cannabinoid CB2 receptors Pietro Marini, Maria-Geazia Cascio, Angela King, Roger Pertwee, and Ruth Ross.
Journal of Agricultural and Food Chemistry 2015 (9 Pages) Characterization of Lignanamides from Hemp (*Cannabis sativa* L.) Seed and Their Antioxidant and Acetylcholinesterase Inhibitory Activities Xiaoli Yan, Jiajing Tang, Carolina Dos Santos Passos, Alessandra Nurisso, Claurdia Avello Simoes-Pires, Mei Ji, Hongxiang, and Peihing Fan. Department of Natural Product Chemistry, Key Laboratory of Chemical Biology of Ministry of Education, School of Pharmaceutical Sciences, Shandong University, Jinan 250012, China.
Science Direct 2005 (10 Pages) Chemical constituents of marijuana: The complex mixture of natural cannabinoids Mahmoud A. Elsohly ANF Desmond Slade. National Center for Natural Products Research, School of Pharmacy, The University of Mississippi, University, MS 38677.
Journal of Liquid Chromatography and Related Technologies 2005 (24 Pages) Chromatographic and Spectroscopic Data of Cannabinoids from *Cannabis sativa* L. Arno Hazekamp, Anja Pelentburg, and Rob Verpoorte Division of Pharmacognosy, Institute of Biology, Leiden University, Leiden, The Netherlands.
Cannabis and Cannabinoid Research 2017 (12 Pages) Chronic Adolescent D9-TetrahydrocannabinolTreatment of Male Mice Leads to Long-Term Cognitive and Behavioral Dysfunction, Which Are Prevented by Concunrent Cannabidiol Treatment Michelle Murphy, Sierra Mills, Joanna Winstone, Emma Leishman, Jim Wager-Miller, Heather Bradshaw, and Ken Mackie Program in Neuroscience, Dep of Counseling & Educational Psychology, Dep of Psychological and Brain Sciences, and Gill Center, IN University, Bloomington, IN.
Cold Pressing and Supercritical CO Extraction of Hemp 2014 (10 Pages) K. Aladic, S. Jokie, T. Moslavac, S. Tomas, S. Vidovic, J. Valdic, and D. Subaric.
Toxicology and Applied Pharmacology Comparison of Acute Oral Toxicity of Cannabinoids in Rats, Dogs and-Monkeys 1973 (10 Pages) George Thompson, Harris Rosenkrantz, Ulrich Schaeppi, and Monique Bradude.
Scientific Report Consumers Prescriptions of Hemp Products for Animals 2016 (9 Pages) Colorado State University, Fort Collins, CO Lori Kogan, Peter Hellyer, and Narda Robinson.
Journal of Analytical Toxicology 2000 (5 Pages) Rockville, Maryland T.Z. Bosy and K.A.Cole.
Frontiers in Pharmacology 2016 (19 Pages) Los Angeles Current Therapeutic Cannabis Controversies and Clinical Trial Design Issues Ethan B. Russo.
Cannabis and Cannabinoid Research 2016 (10 Pages) Decarboxylation Study of Acidic Cannabinoids: A Novel Approach Using Ultra-High-Performance Supercritical Fluid Chromatography/Photodiode Array-Mass Spectrometry Mei Wang, Yan-Hong Wang, Mohamed M. Radwan, Amirs Anas, John Antwerp, Jon Parcher, Mohmoud Elsholy, and Ikhlas Khan.
Hemp seed oil A source of valuable essential fatty acids 2017 (6 Pages) Brig, Switzerland Jean-Luc Deferne and David W. Pate.

(56) References Cited

OTHER PUBLICATIONS

Determination of cannabinoids in hemp food products by use of headspace solid-phase microextraction and gas chromatography—mass spectrometry 2004 (8 Pages) Dirk W. Lachenmeier, Lars Kroener, Frank Musshoff, and Burhard Madea.

Waters the Science of What's Possible Forced Degradation of Cannabidiol Waters Corporation, Milford, MA USA Catharine Layton, Jacquelymrunco, and Andrew Aubin.

Dietary fats and pharmaceutical lipid excipients increase systemic exposure to orally administered cannabis and cannabis-based medicines 2016 (12 Pages) Atheer Zgair, Jonathan Wong, Jong Bong Lee, Jatin Mistry, Olena Sivak, Kishor Wasan, Ivo Hennig, David Barrett, Cris Constantinescu, Peter Fischer, and Pavel Gershkocinch.

Frontiers in Psychiatry Does Cannabidiol protect against adverse psychological effect of THC? 2013 (8 Pages) Heerlen, Netherlands Raymond J.M. Niesink and Margriet Van, Laar.

Downregulation of prejunctional CB1 and CB2 cannabinoid receptors and TRPV1 channels is involved in the impaired neurogenic contraction of bladder in insulin-resistant obese Zucker rat 2015 (1 Page) Madrid, Spain Blaha Recio, Martinez M.P, Fernades V., Lopez-Olivia, Reberios A.S., Bustamante, Carballido, Prieto, Garcia Sacristan, Hernandez.

British Journal of Pharmacology 2000 (9 Pages) Palo Alto, California Eects of cannabinoid receptor agonists on neuronally-evoked contractions of urinary bladder tissues isolated from rat, mouse, pig, dog, monkey and human R.S. Martin, L.A. Luong, N.J Welsh, R.M. Eglen, G.R. Martin and S.J. Maclennan.

Pharmacology and Toxicology 2006 (8 Pages) Kaohsiung, Taiwan Effect of Anandamide on Cytosolic Ca2rr Levels and Proliferation in Canine Renal Tubular Cells Jeng-Hsien Yeh, He-Hsiung Cheng, Chaing-Ting Chou, and Chung-Ren Jan.

British journal of Pharmacology 2008 (11 Pages) Effect of D9-tetrahydrocannabinol, a cannabinoid-receptor agonist, on the triggering of transient lower oesophageal sphincter relaxations in dogs and humans. H Beamount, J Jensen, A Calsson, M. Ruth, A Lehann, and GE Beockxstaens.

Toxicology Sciences 2011 (9 Pages) Effect of Developmental Chlorpyrifos Exposure, on Endocannabinoid Metabolizing Enzymes, in the Brain of Juvenile Rats Russel L. Carr, Abodolsamad Borzajani, and Mattew K. Ross.

Hindawi Publishing Corporation Journal of Veterinary Medicine 2013 (9 Pages) Effects of Essential Oils and Polyunsaturated Fatty Acids on Canine Skin Equivalents: Skin Lipid Assessment and Morphological Evaluation S. Cerrato, L. Ramio-Lluch, D. Rodes, R Brazis, and A. Puigdemont.

Effects of hempseed and flaxseed oils on the profile of serum lipids, serum total and lipoprotein lipid concentrations and haemostatic factors 2006 (8 Pages) Ursula S. Schwab, James C. Callaway, Arja T. Erkkila, Jukka Gynther, Matti I.J. Uusitupa, Tomi Jarvinen.

Journal of Dermatological Treatment. 2005 (8 Pages) Efficacy of dietary hempseed oil in patients with atopic dermatitis James Callawayursula Schwab, Ilkka Harvima, Pirjo Halonen, Otto Mykkanen, Pekka Hyvonen and Tomi Jarvinen.

European Food Safety Authority (41 Pages) Scientific Opinion on the safety of hemp (*Cannabis* genus) for use as animal feed1 EFSA Panel on Additives and Products or Substances used in Animal Feed (FEEDAP).

NIH Public Access 2010 (24 Pages) Endocannabinoid Signaling in Neurotoxicity and Neuroprotection C.Pope, R.Mechoulam, and L. Parsons.

Heart and Circulatory Physiology 2016 (67 Pages) Budapest, Hungary Endocannabinoids in Ceverbroacualr Regulation Zotan Benvo, Eva Ruisanchez, Mirian Lesz-Ishiauro, Peter Sandor, and Pal Pacher.

Endocannabinoids in the Retina: From Marijuana to Neuroprotection 2008 (55 Pages) Stony Brook, New York Stephen Yazulla.

HHS Public Access Epigenetic Regulation of Immunological Alterations Following Prenatal Exposure to Marijuana Cannabinoids and its Long Term Consequences in Offspring 2015 (18 Pages) Columbia, SC Elizabeth E. Zumbrun, Jessican M. Sido. Prakash S. Nagarkatti, and Mitzi Nagarakitti.

2016 American Chemical Society and American Society of Pharmacognosy the Journal of Natural Products (8 Pages) Wald-Schönengrund, Switzerland Oier Aizpurua-Olaizola, Umut Soydaner, Ekin Ozturk, Daniel Schibano, Yilmaz Simsir, Patricia Navarro, Nestor Etxebarria, and Arestaz Usobiaga.

Food Chemistry and Toxicology 2003 Institute of Food Technologists (4 Pages) Fatty Acid Composition and Oxidative Stability of Cold-pressed Edible Seed Oils T.D. Parker, D.A. Adams, K. Zhou, M. Harris, and L. Yu.

Federal Register / vol. 81, No. 240 / Wednesday Dec. 14, 2016 / Rules and Regulations.

Five CommonToxins Ingested by Dogs and Cats 2008 (11 Pages) Julie Ann Luiz University of Hawaii at Hilo Johanna Heseltine Oklahoma State University.

The Journal of Physical Chemistry Flexible Bionanocomposites from Epoxidized Hemp Seed Oil Thermosetting Resin Reinforced with Halloysite Nanotubes Peter S. Shuttleworth, Ana M. Diez-Lascual, Carlos Marco, and Gary Ellis Institute of Polymer Science and Technology, CSIC, c/Juan de la Cierva 3, 28006 Madrid, Spain.

Food Protein-Derived Bioactive Peptides: Production, Processing,and Potential Health Benefits 2012 Journal of Food and Science Chibukie C. Udengiwe and Rotimi E. Aluko.

Water's The Science of What's Possible Food Protein-Derived Bioactive Peptides: Production, Processing, and Potential Health Benefits Chibukie C. Udengiwe and Rotimi E. Aluko.

Hempseed as a Functional Food 2016 23rd Annual Conference of the HIA Jace Callaway.

Indian Journal of Urology Functional Role of Cannabinoid Receptors in Urinary 2010 Pittsburgh, PA Pradeep Tyagi, Vikas Tyagi, Naoki Yoshiare, and Muchael Chacellor.

The Journal of Pharmacology and Experimental Therapeutics Functional Selectivity of CB2 Cannabinoid Receptor Ligands at a Canonical and Noncanonical Pathways Amet Dhopeeshwalker and Ken Mackie The Gill Center for Biomolecular Science and the Department of Psychological and Brain Sciences, Indiana University, Bloomington, Indiana Received Jan. 30, 2016; accepted May 17, 2016.

Journal of Analytical Toxicology GC-MS Analysis of the Total Ag-THC Content of Both Drug- and Fiber-Type Cannabis Seeds Samir A. Ross, Zlatko Mehmedic, Tmothy P. Murphy, and Mohmoud A. Elsohly 1National Center for Natural Products Research, Research Institute of Pharmaceutical Sciences; Departments of Pharmacognosy 2 and Pharmaceutics 3, School of Pharmacy, University of Mississippi, University, MS 38677 and 4ElSohly Laboratories, Incorporated (ELI) 5 Industrial Park Drive, Oxford, MS 38655.

J Forensic Sci, Mar. 2006, vol. 51, No. 2 Genetic Variation in Hemp and Marijuana (*Cannabis sativa* L.) According to Amplified Fragment Length Polymorphisms Shannon L. Datwyler Ph.D. and George D. Weiblen Ph.D.

Public Health in-the 21st Century *Cannabis sativa* for Health and Hemp Ethan L. Clark.

Health Canada Information for Health Care Professionals Cannabis (marihuana, marijuana) and the cannabinoids Prepared by Health Canada Date of latest version: Feb. 2013.

Journal of Nutrition and Metabolism 2012 Health Implications of High Dietary Omega6 Polyunsaturated Fatty Acids E. Patterson, R. Wall, G.F Fitzgerald, R.P. Ross, and C. Stanton Alimentary Pharmabiotic Centre, Biosciences Institute, County Cork, Ireland Teagasc Food Research Centre, Biosciences Department, Moorepark, Fermoy, County Cork, Ireland Department of Microbiology, University College Cork, County Cork, Ireland C. Stanton Academic Editor: Remy MeierReceived Jul. 28, 2011; Revised Nov. 17, 2011; Accepted Nov. 20, 2011.

Heat generates oxidized linoleic acid metabolites that activate TRPV1 and produce pain in rodents Amol M. Patwardhan, Armen N. Akopian, Kikita B. Ruparel, Anibal Dogenes, Susan T. Weintrabub, Charis Uhlson, Robert C. Murphy, and Kenneth M. Hargeaves. Department of Endodontics, 2Department of Cellular and Structural Biology, and Department of Biochemistry, University of Texas Health Science Center at San Antonio, San Antonio, TX Dep of Pharmacology, Univ of Colorado Health Sciences Center, Denver, CO.

(56) References Cited

OTHER PUBLICATIONS

Hemp—Biochemical Diversity and Multiple Uses Elena Try, Tefania Surdu, Maria Rou, and Maria Asaf 2009 (8 Pages).

Journal of Agricultural and-Food Chemistry Hemp (*Cannabis sativa* L.) Seed Oil: Analytical and Phytochemical Characterization of the Unsaponifiable Fraction S. Montserrat-De La Paz, F. Marin-Aguilar, M.D. Garcia-Gimenez and M.A. Fernandez-Arche Department of Pharmacology, Faculty of Pharmacy, University of Sevile, 41012 Seville, Spain Laboratory of Cellular and Molecular Nutrition, Instituto de la Grasa, Spanish National Research Council (CSIC), 41012 Seville, Spain.

Congressional Research Service Hemp as an Agricultural Commodity Renee Johnson 2017.

Colorado State University Research and Development of Hemp Genetics John McKay.

* cited by examiner

PET FOOD INCLUDING CANNABIDIOLIC ACID

FIELD OF THE INVENTION

The present invention pertains to food products containing cannabinoids, and particularly to canine and feline food products including acid-form cannabinoids.

BACKGROUND OF THE INVENTION

Cannabinoids are substances capable of activating receptors in the endocannabinoid system of many animals including humans. Over a hundred different cannabinoids can be isolated from *cannabis* and these each exhibit varied effects.

Classical cannabinoids, as defined herein, are Tetrahydrocannabinol (THC), Tetrahydrocannabinolic acid (THC-A), Cannabidiol (CBD) and Cannabidiolic acid (CBD-A), although many other cannabinoids have been well documented and researched. The acid forms of theses classical cannabinoids predominate in the *Cannabis sativa* plant and other plants.

The seeds of the *Cannabis sativa* plant are rich in essential fatty acids, that are beneficial in animals including humans. These fatty acids are associated with reduction in inflammation and may address other health issues including obesity. Seeds of *Cannabis sativa*, namely industrial hemp, are often cold pressed to extract oils rich in essential fatty acids.

The flowers, leaves, seeds, stalks and stems of *Cannabis sativa* can be processed to extract oils containing various cannabinoids. The stems, leaves and seeds contain detectable amounts of certain cannabinoids. Cannabinoids and essential fatty acids, are known to have health benefits, including the reduction of inflammation.

Cannabidiol (CBD) is the most abundant classical cannabinoid in hemp oil (making up over 90% of the cannabinoid content). CBD has little affinity for CB1 or CB2 receptors, which are the main points of interaction for cannabinoids in the endocannabinoid system. CBD does act as an antagonist of cannabinoid agonists and thus has an indirect effect on the endocannabinoid system. CBD may temper the "high" caused by THC. CBD includes CBD-C1: Cannabidiol-C1, CBD-C4: Cannabidiol-C4, and CBD-A: Cannabidiolic Acid.

Cannabigerol is a precursor to other cannabinoids. Most CBG is transformed into other cannabinoids like CBD or THC by the plant or through other external processes. Natural CBG levels are very low in most *cannabis* plants and has been isolated in its acid and non-acid forms.

Tetrahydrocannabinol is an abundant classical cannabinoid found in most medical and recreational marijuana strains. THC mimics the action of anandamide, a neurotransmitter naturally produced in the human body, and binds to CB1 receptors in the endocannabinoid system found mostly in the brain. However, in industrial hemp THC is a minor constituent and appears only in trace amounts under 3000 ppm (0.30%) by dry weight, as required by the regulations of many countries. Hemp oil derived from industrial hemp is non-psychoactive—due to its low THC content. THC has numerous forms and iso-forms including acid and non-acid forms. Examples include: THC-A-A: Delta-9-tetrahydrocannabinolic Acid A, THC-A-C 1: Delta-9-tetrahydrocannabiorcolic Acid, THC-A-C4: Delta-9-tetrahydrocannabinolic Acid C4, THC-A-B: Delta-9-tetrahydrocannabinolic Acid B, THC-C 1: Delta-9-tetrahydrocannabiorcol, THC-C4: Delta-9-tetrahydrocannabinol C4, iso-THC: iso-Tetrahydrocannabinol.

Cannabinol results from the degradation of THC. There is little Cannabidiol in the fresh plant, but decarboxylation often raises the amount of CBN in the plant. CBN is only mildly psychoactive and has a higher affinity for the CB2 receptor than the CB1 receptor, linking CBN to the body's immune system. In hemp oil, CBN is present in levels of 2000 ppm (0.2%) or lower. Other forms can include: CBN-C1: Cannabiorcol, CBN-C2: Cannabinol-C2, CBN-C4: Cannabinol-C4, CBND: Cannabinodiol.

Along with the primary cannabinoids and their variants, there are a number of minor cannabinoids whose benefits have not yet been thoroughly studied. Even in low quantities, these cannabinoids may interact with the endocannabinoid system and some of these minor cannabinoids include: CBC: Cannabichromene, CBL: Cannabicyclol, CBT: Cannabitriol, CBE: Cannabielsoin, CBR: Cannabiripsol, DCBF: Dehydrocannabifuran, CBF: Cannabifuran, CBCN: Cannabichromanon, and CBT: Cannabicitran. These minor cannabinoids, may be associated with the "Entourage Effect".

Like THC-A and CBD-A, there are other non-decarboxylated forms of cannabinoids present in *cannabis*. Once exposed to heat, light, or alkaline conditions, these cannabinoids lose a carboxyl group. The following acidic cannabinoids are typically found in *Cannabis*: CBCA: Cannabichromenic Acid, CBL-A: Cannabicyclolic Acid, CBEA-A: Cannabielsoic Acid A, CBEA-B: Cannabielsoic Acid B, CBNA: Cannabinolic Acid.

The "varin" type cannabinoids have the suffix -varin in their names. These differ in length from common cannabinoids, replacing the typical 5 carbon chain with a 3 carbon chain. These include: CBV: Cannabivarin, THCV: Tetrahydrocannabivarin, CBDV: Cannabidivarin, CBCV: Cannabichomevarin, CBGV: Cannabigerovarin, CBLV: Cannabicyclovarin, CBVD:

Cannabinodivarin, CBTV: Cannabitriolvarin.

The following acidic forms of varin type cannabinoids are non-decarboxylated: CBGV-A: Cannabigerovarinic Acid, THCVA: Delta-9-tetrahydrocannabivarinic Acid, CBDVA: Cannabidivarinic Acid, CBCVA: Cannabichromevarinic Acid.

Various ether form cannabinoids have been discovered. These include: CBG-AM: Cannabigerolic Acid Monomethyl Ether, CBGM: Cannabigerol Monomethyl Ether, CBDM: Cannabidiol Monomethyl Ether, CBNM: Cannabinol Methyl Ether, CBTVE: Ethoxy-cannabitriolvarin. While trace quantities of these ether form cannabinoids found in hemp oil, some believe that these ether form cannabinoids are partially responsible for the entourage effect and may influence bio-activity of the other cannabinoids.

The endocannabinoid system includes receptors that bind cannabinoids. CB1 and CB2 are well-documented receptors for cannabinoids. The CB1 receptors are present in the brain. The CB2 receptors are not fully mapped but are believed to be concentrated in the immune and hematopoietic systems. Cannabinoids can cause biological effects by binding to these and to additional receptors.

The endocannabinoid system also includes enzymes that make or degrade endocannabinoids from arachidonate-based lipids. Agonistic activity by endocannabinoids on the CB1 and CB2 receptors yields many well-documented health benefits.

Phytocannabinoids are plant-derived cannabinoids that modulate the endocannabinoid system. Although phytocannabinoids are found in many plants, the highest, known concentrations are found in *Cannabis sativa*. Common names for the well-known varieties in the *cannabis* family are hemp and marijuana. The most abundant acidic classical phytocannabinoids typically found in freshly harvested *Cannabis sativa* are Tetrahydrocannabinolic acid (THC-A) and Cannabidiolic acid (CBD-A), although others also exist.

The term phytocannabinoids should be broadly understood to refer to any plant derived compound that affects the cannabinoid regulatory system and found in *Cannabis sativa* or other plants. In addition to the classical cannabinoids, phytocannabinoids also include some terpenes (e.g. caryophyllene), alkylamides (e.g. isobutylamide) and polyynes (e.g. falcarinol).

According to some research, CBD has minimal affinity for CB1 or CB2 receptors, and may act as an indirect antagonist of cannabinoid agonists.

CBD may also be a 5-HT1a and 5-HT2a receptor agonist. Interactions between receptors and cannabinoids are continually being discovered. As the science evolves there is mounting evidence that the ability of being able to select and optimally deliver a preferred cannabinoid mixture is desirable. Recent research provides surprisingly beneficial health effects achieved through the utilization of micro doses of cannabinoids on a regular basis for long continuous periods, i.e. several months.

The term "entourage effect" is applicable to cannabinoids because combinations of cannabinoids have been found to be more bioactive than individual cannabinoids.

While the health benefits of consumption of phytocannabinoids are well documented, there are drawbacks of smoking *cannabis*. Many medical marijuana patients prefer edibles over smoked marijuana because smoking is not typically associated with improved health and may aggravate certain health conditions. Unfortunately, intense processing of edibles is especially common. In particular, many edibles that include cannabinoids are cooked, pasteurized, sterilized, baked, heat dried, or extruded. These processes will typically convert a significant portion of the classical cannabinoids from their acidic forms to into the non-acidic decarboxylated forms.

Edible *cannabis* infused products include *cannabis* extracts as an ingredient. However, the processes used to extract the cannabinoids may also convert a high percentage of the naturally occurring acid forms of the primary phytocannabinoids into non-acid forms through the process of decarboxylation. Decarboxylation causes THC-A, for example, to convert to THC. THC is associated with increased psychoactive effects when compared to its precursor THC-A. While THC may occur naturally, decarboxylation of cannabinoids, including THC-A and CBD-A can occur by various mechanisms. While there are many health benefits to both acid and non-acid forms of these molecules, acidic cannabinoids have different pharmacologies and therapeutic effects than the decarboxylated forms.

According to some researchers, there are limits to the rate that fully decarboxylated THC that can be absorbed by the body. Since THC-A and CBD-A have different pharmacologies than their decarboxylated counterparts, it's preferable to control the amounts of acidic and non-acidic cannabinoids in edible products.

Many cannabinoids, including terpenes, are volatile or unstable in the presence of heat or intense processing. Current ways of processing and delivering cannabinoids through food products may volatilize or change the molecular structures of some cannabinoids. Accordingly, an intensely processed food with cannabinoids in an oil may have different therapeutic outcomes than a less processed food.

Typically, products derived from hemp that contain less than 3000 ppm (0.30% dry weight) of tetrahydrocannabinoids are exempt from the legal definition of marijuana in the United States, for example.

U.S. Pat. No. 7,399,872 to Mechoulam et al. describes a way of converting CBD into THC under lab conditions using a specialized reaction mixture an organic solvent and $NaHCO_3$. There is anecdotal evidence that similar reactions may occur in the gastric juice of humans. Gastric juice, or gastric acid, contains hydrochloric acid (HCl), potassium chloride (KCl) and sodium chloride (NACl) along with numerous enzymes that are activated by these acids. Molecules including CBD may convert into THC in the presence of gastric acid.

While the amount of CBD that may convert to THC under gastric conditions may be small, some consumers may wish to consume products that are less capable of producing THC.

Patients may also prefer that their medical marijuana be optimized for potency through the entourage effect by the full inclusion of the naturally occurring array of cannabinoids. Further, cannabinoids in the acid forms are preferred because the higher therapeutic doses are possible without negative side effects such as psycho activity. A patient can typically tolerate higher and more effective doses of cannabinoids without the psychoactive side effects associated with the decarboxylated (non-acid) forms.

What is desired is: 1) food manufacturing processes that yield functional foods having micro-doses of cannabinoids and that enable an entourage effect in vivo, 2) functional foods that predominately include acidic forms of cannabinoids. 3) food manufacturing processes that yield food products for humans or animals, where the food products have a more controlled composition of cannabinoids, 4) food products that include predominately the acid-form of at least one desired cannabinoid.

SUMMARY OF THE INVENTION

Edible oils are ingredients included in many, if not most, packaged foods. Common edible oils include olive oil, rapeseed oil, sunflower oil, corn oil, tallow, lard, chicken fat, and soybean oil. These can be supplemented with cannabinoids because cannabinoids exhibit a high degree of solubility in these edible oils. Since edible oils are also used in many food products, edible oils can be used as a carrier to add cannabinoids to edible products without significantly changing a recipe or without adversely influencing flavor. Some edible oils (i.e. hemp oil) naturally contain phytocannabinoids.

One drawback of traditional food processing methods is that heat is typically applied during the manufacture of packaged food products. Cannabinoids can react during production of food products in the presence of heat which changes the composition of the cannabinoids. The present invention includes products and methods for adding combinations of edible oils and cannabinoids that minimize changes in the composition of cannabinoids in certain edible products including extruded food products, baked food products, nut butters, spreads, pourable dressings, pelleted feeds, cold sausages and many other processed foods.

In one embodiment of the invention an extruded food product includes a food substrate manufactured by a hot extrusion process and having a cannabinoid mixture. The hot extrusion process is typically performed at above 80° C.

In another embodiment of the invention, a pet food product manufactured by extrusion or another method includes a food substrate having a blended combination of edible oils including a cannabinoid mixture. The first oil is hemp oil having cannabidiolic acid (CBD-A), and tetrahydrocannabinol (THC). The THC has a concentration of less than 100 ppm in the hemp oil. The THC and the CBD-A comprise primary functional components of the cannabinoid mixture.

Preferably, the hemp oil is cold pressed having a ratio of CBD-A to THC that is at least 1:3. It can be appreciated that an alternate embodiment has the same ratio replacing the CBD-A with CBD. In a further embodiment, the ratio of the combination of CBD and CBD-A to THC is at least 1:3

It can be appreciated that an alternate embodiment has the ratio of CBD-A to THC-A that is at least 1:3. In a further embodiment, the ratio of at least 1:3 comprises the combination of CBD and CBD-A, to the combination of THC and THC-A.

The pet food product includes a second oil being blended with the hemp oil to inhibit oxidation of the CBD-A and THC-A, non-acid forms of these molecules, other cannabinoids, and combinations thereof. The blended combination of hemp oil and the second oil are applied to the food substrate and do not exceed 10% of the pet food product by weight.

The cannabinoid mixture particularly includes primarily non-decarboxylated cannabinoids selected from the group consisting of A-9-tetrahydrocannibolic acid (THC-A), A-9-tetrahydrocannibolic acid (THC-B), A-9-tetrahydrocannibolic acid-$C_4$ (THC-A-$C_4$), A-9-tetrahydrocannibivarinic acid, A-9-tetrahydrocannibiorcolic acid (THC-A-C1), A-8-tetrahydrocannibolic acid (g-THC-A), cannabicyclolic acid (CBL-A), cannabidiolic acid (CBD-A), cannabigerolic acid (DBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabigerolic acid A monomethyl ether (CBG-AM-$0_5$ A) and cannabinolic acid (CBNA), and combinations thereof.

The food substrate may also include decarboxylated cannabinoids selected from the group consisting of CBD, THC and combinations thereof. This can be due to natural decarboxylation over time, or due to the natural occurrence of the decarboxylated forms in the live plant material, or other factors that are not controlled. Preferably the cannabinoids are primarily in the non-decarboxylated forms.

In one embodiment of the invention, the ratio by weight of Cannabidiolic Acid to cannabidiol is greater than 1:1. Preferably the ratio is greater than 3:1. In one embodiment the ratio is greater than 9:1. In another embodiment of the invention, the ratio by weight of Tetrahydrocannabinolic acid (THC-A) to Tetrahydrocannabinol (THC) is greater than 1:1. In one embodiment, the ratio is greater than 9:1.

The cannabinoid mixture further may include added phytocannabinoids, such as terpenes, alkylamides and terpenes, carotenoid, phenolic compounds and phytosterols to quench oxygen and to scavenge free radicals thereby reducing oxidation of Cannabidiolic Acid, and other classical cannabinoids and to optimize entourage effects.

The cannabinoid mixture is added to the food substrate after the food substrate is extruded, and after it cools to below 80° C. This relatively low temperature minimizes the degradation or volatilization of many of these other phytocannabinoids. Table 1 shows tested ratios of CBD-A:CBD, CBD-A:THC and CBD:THC in various hemp oil samples.

TABLE 1

| CBD-A:CBD | CBD-A:THC | CBD:THC |
|---|---|---|
| 3.69 | 1.88 | 0.510051 |
| 1.99 | 2.01 | 1.010101 |
| 2.51 | 2.69 | 1.070107 |
| 6.74 | 2.36 | 0.350035 |
| 3.00 | 2.97 | 0.990099 |

According to Table 1, the ratio of CBD-A:CBD is between approximately 2:1 and 7:1. The ratio varies because many hemp oils have varying ratios.

The ratio of CBD-A:THC varies between approximately 2:1 and 3:1. The ratio of CBD:THC varies between approximately 1:2 and 1:1 in the examples provided in Table 1. It can be appreciated that these ratios are examples only and the ratios can vary or be modified as desired.

In an alternative embodiment, the cannabinoid mixture is mixed with edible oil and added to the food substrate prior to a cold extrusion process. Preferably, the edible oil includes significant concentrations of omega-3 fatty acids. Preferably, the edible oil can include a portion of hemp oil, flax seed oil, or other oil rich in omega-3 fatty acids.

The food product in one embodiment is pasta, a breakfast cereal product, a snack bar, or a pet food formed into kibbles. It can be appreciated that the process and product described herein can be formed into any of a variety of food products.

In one embodiment of the invention, the cannabinoid mixture includes cannabinoids selected from the group consisting of, cannabigerol, cannabichromene, cannabicyclol, cannabivarian, tetrahydrocannabivarin, cannabidivarin, cannabichromevarin, cannabigerovarin, cannabigerol monomethyl ether, and combinations thereof. These cannabinoids may be in their acid forms, non-acid forms, or combinations thereof. These phytocannabinoids can be derived from *Cannabis sativa*, other plants, or synthetically derived.

In another embodiment, the extruded food product is manufactured by the hot extrusion process at temperatures greater than 80° C. The extruded food product is cooled to 80° C. or below, and the cannabinoid mixture is added after the step of cooling to inhibit decarboxylation of any component of the cannabinoid mixture. It can be appreciated that there still may be an inconsequential degree of decarboxylation but that an optimal ratio can be maintained.

While the cannabinoids can be derived from numerous sources, the ideal cannabinoid mixture is derived from a whole plant extracts of *Cannabis sativa*. More preferably, the cannabinoid mixture is derived solely from hemp having a THC concentration of less than 3000 ppm (0.3% by dry weight) as measured on a dry weight basis.

The edible oil including the cannabinoid mixture coats the food substrate through mixing. In another embodiment, the cannabinoid mixture coats the food substrate by spraying. In another embodiment, the cannabinoid mixture coats the food substrate by dipping or bathing.

The edible oil including the cannabinoid mixture is processed to inhibit microbial contamination. This process is selected from the group consisting of: irradiation, filtration, pressure treatment, bactericide addition, antibiotic addition, or combinations thereof, in a way that does not significantly decarboxylate the acid forms of cannabinoids. The edible oil processing maintains the desired ratio by weight of any one non-decarboxylated phytocannabinoid to its decarboxylated phytocannabinoid form of greater than 9:1 and possibly up to the ratio naturally found in freshly harvested natural

*cannabis* biomass, or any ratio greater than 9:1. To inhibit decarboxylation of the cannabinoids the edible oil including the cannabinoid mixture does not exceed a temperature of 80° C. at any time during processing according to one embodiment of the invention.

Ideally the cannabinoid mixture further includes terpenes and alkylamides to enable a desired entourage effect. It may optionally further include polyynes. It can be appreciated that the cannabinoid mixture can be pre-determined and optimized to achieve the desired concentrations of cannabinoids. Preferably, the terpenes and alkylamides are derived from *Cannabis sativa*. It can be appreciated that where a desired cannabinoid mix is determined, various terpenes, alkylamides and polyynes can be added to fortify the cannabinoid mixture. It can be further appreciated that other phytocannabinoids can be added to fortify the cannabinoid mixture. Lastly it can be appreciated that cannabinoids derived from any source, natural or synthetic, can be added to fortify the mixture. These can be derived from any source, including plants such as *Cannabis sativa*.

The present invention encompasses dry packaged food products, including baked goods, snacks, breads, muffins, cakes and cookies. Many of these are cooked or otherwise dehydrated to a moisture content of less than 15% by weight to inhibit spoilage, maximize shelf life, and conform to modern taste preferences. The dry food substrate having a cannabinoid mixture including, non-decarboxylated phytocannabinoids including those selected from the group consisting of A-9-tetrahydrocannibolic acid (THC-A), A-9-tetrahydrocannibolic acid (THC-B), A-9-tetrahydrocannibolic acid-$C_4$ (THC-A-$C_4$), A-9-tetrahydrocannibivarinic acid, A-9-tetrahydrocannibiorcolic acid (THC-A-$C_1$), A-8-tetrahydrocannibolic acid ($A^8$-THC-A), cannabicyclolic acid (CBL-A), cannabidiolic acid (CBD-A), cannabigerolic acid (DBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabigerolic acid, A monomethyl ether (CBG-AM-$0_5$ A) and cannabinolic acid (CBNA), and combinations thereof.

The dry food substrate includes decarboxylated phytocannabinoids including those selected from the group consisting of CBD, THC, and combinations thereof. In one embodiment, the dry packaged food products include only non-decarboxylated cannabinoids.

Optimally, the ratio by weight of non-decarboxylated phytocannabinoids to decarboxylated phytocannabinoids is greater than 1:1. Preferably the ratio is greater than 3:1. In another embodiment there are no decarboxylated cannabinoids.

While some embodiments of the present invention utilize CBD-A and TCH-A, it can be appreciated that a variety of acidic cannabinoids can be utilized in accordance with the present invention. Although particular genetics, and growing conditions, can be adapted to produce any of a variety of cannabinoid profiles, it is expected that certain cannabinoids and other components can be extracted and re-combined in optimal concentrations to achieve the goals of the present invention.

The dry packaged food product is baked, or otherwise cooked. The cannabinoid mixture is dissolved into an edible oil. This edible oil may be sprayed or otherwise applied to the food substrate. In one embodiment, the edible oil impregnates the food substrate. In another embodiment, the cannabinoid mixture dissolves into, or is mixed with, the edible oil and at least partially coats the food substrate.

Preferably the edible oil is pre-processed to inhibit microbial contamination by a process selected from the group consisting of: irradiation, filtering, pressure treatment, or combinations thereof. More preferably, the cannabinoid mixture and the edible oil are processed together in a way that does not significantly modify the ratio of non-decarboxylated to decarboxylated classical cannabinoids.

In a variation of this embodiment, the cannabinoid mixture and edible oil are processed to inhibit microbial contamination In an embodiment of the invention, the edible oil including the cannabinoid mixture does not exceed a temperature of above 80° C. during processing to inhibit significant modification of the cannabinoids and to maintain the ratio.

A variation of the invention includes an edible oil product. This can be distributed to food manufacturers for use in packaged food products. The edible oil product includes a cannabinoid mixture. The cannabinoid mixture includes predominately acidic cannabinoids.

The edible oil product is processed to inhibit microbial and pathogenic contamination and to assure food safety. This process can be applied to the combined edible oil and cannabinoid mixture in a way that does not significantly change the amount of acidic-cannabinoids in the edible oil. In another embodiment this process can be applied to the edible oil and the cannabinoid mixture separately, prior to combination of the edible oil and the cannabinoid mixture. In this way, the edible oil can be processed in conventional ways, and the cannabinoid mixture can be processed in a way that optimizes the stability of the acidic cannabinoids, and other cannabinoids including terpenes.

The edible oil is preferably processed by a method selected from the group consisting of: irradiation, filtering, pressurization, or combinations thereof. This process inhibits microbial and pathogenic contamination and thereby preserves the edible oil, improving its shelf life and stability.

Various edible oils are available for utilization with the present invention. In one embodiment the edible oil is included in a nut butter. Preferably, this is simply mixed with the edible oil containing the cannabinoid mixture. The product is a cannabinoid infused nut butter that is shelf stable. In this embodiment, the nut butter is pre-processed to eliminate microbial and pathogenic contamination.

In another embodiment, the mixture of nut butter and the edible oil including the cannabinoid mixture is preserved by a process selected from the group consisting of: irradiation, filtering, pressurization, or combinations thereof.

The invention includes a liquid food product such as a condiment spread that includes other edible oil mixed with hemp oil having cannabinoids.

The cannabinoid mixture includes non-decarboxylated phytocannabinoids selected from the group consisting of CBD-A, TIIC-A, and combinations thereof. The food substrate including decarboxylated phytocannabinoids selected from the group consisting of CBD, THC, and combinations thereof. In another embodiment, the non-decarboxylated phytocannabinoids are chosen from those described in this patent application, and combinations thereof.

The ratio by weight of non-decarboxylated (acid form) phytocannabinoids to decarboxylated (non-acid form) phytocannabinoids is greater than 1:1.

The cannabinoid mixture is dissolved into another edible oil, which is mixed with the food substrate at a temperature of less than 80° C. during manufacture to inhibit decarboxylation of the cannabinoids in the cannabinoid mixture. Preferably, the cannabinoid mixture contains predominately acidic cannabinoids and contains minimal amounts of THC, Preferably, the cannabinoid mixture is directly extracted from the *Cannabissativa* plant and has a cannabinoid mix that is reflective of the naturally occurring cannabinoid mix found in the plant. It can be appreciated that the cannabinoid mixture can contain supplemental cannabinoids that are added. The cannabinoid mixture can be derived from isolated and/or synthesized cannabinoids that are separated, then remixed in a formulation according to a pre-determined combination of cannabinoids to achieve desirable therapeutic results and improved product consistency.

In one embodiment of the invention, a pet food product includes a baked or extruded food substrate. The food product further includes hemp oil having cannabidiolic acid (CBD-A) concentration of between 15-55 ppm, and tetrahydrocannabinol (THC). The ratio of CBD-A to THC is at least 1.88:1 in the hemp oil. The food product includes a second oil blended with the hemp oil to inhibit oxidation of the CBD-A. The blended combination of hemp oil and the second oil are applied to the food substrate and do not exceed 10% of the food product by weight.

The invention alternatively includes a pet food product including a baked or extruded food substrate. The food product further includes hemp oil having hemp oil having a cannabidiol (CBD) concentration of between 15-50 ppm, and tetrahydrocannabinol (THC) where the ratio of CBD to THC is at least 0.35:1; in the hemp oil. The food product includes a second oil blended with the hemp oil to inhibit oxidation of the CBD-A. The blended combination of hemp oil and the second oil are applied to the food substrate and do not exceed 10% of the food product by weight.

DETAILED DESCRIPTION

Figure 1:
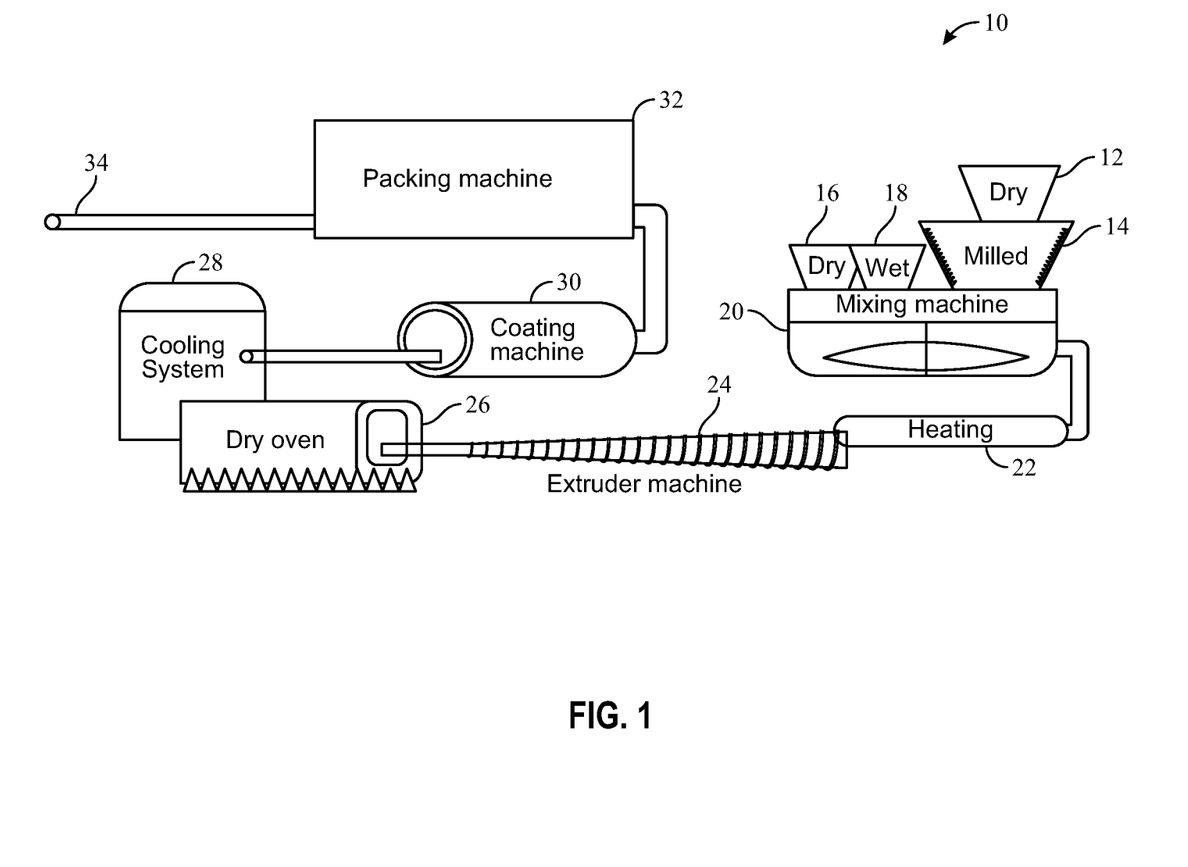
FIG. 1 is an extrusion system in accordance with the present invention.

FIG. 1 is a system in accordance with the present invention, generally designated with the reference numeral 10. The system 10 includes a series of hoppers that feed the mixing machine. There is a primary dry hopper 12 and a primary milled hopper 14 that directly feed primary ingredients into the mixing machine 20. Temperature of the mixing machine can be controlled to deliver desired processing control. The system 10 could further include a secondary dry hopper 16. Liquid ingredients can be premixed in a tank 18 and then pumped into the mixer. Alternatively, liquids are directly pumped into the mixer as separate ingredients. Accordingly, any of a variety of mixed ingredients can be selectively and automatically delivered to the mixing machine 20. The mixing machine 20 produces a food substrate that is further modified by the system and methods of the present invention. In one embodiment, the mixer including a heater and the step of heating 22 occurs simultaneously with the mixer 20. In another embodiment, mixing and heating are accomplished sequentially.

The mixing machine 20 guides the food substrate to an extruder machine 24. The extruder machine 24 includes an auger to compress and move the food substrate through the extruder to yield an extruded food substrate. The extruded food substrate is then moved to a dry oven 26 to remove moisture from the extruded food substrate. Once the moisture is removed the food substrate is conveyed to a cooling system 28 which reduces the temperature of the food substrate to below 80° C. Optionally, the dryer oven and cooling system occur within the same machine. The cooled food substrate is conveyed to a coating machine 30, which is adapted for applying an edible oil and flavors to the cooled food substrate. The coating machine 30 is capable of spraying an edible oil onto a food substrate and thereby coating the food substrate with the edible oil. Ideally the spraying process is optimized to enable absorption of the edible oil into the food substrate. The edible oil includes a cannabinoid mixture.

In one embodiment of the invention the coating machine 30 is equipped with sprayers that uniformly spray the extruded food substrate with the edible oil. In another embodiment, the coating machine 30 includes a fluid bed processor for uniformly coating the extruded food substrate with the edible oil. It can be appreciated that various flavor components can be further sprayed or combined for spraying in accordance with the present invention.

The food substrate moves from the coating machine 30 to a packing machine 32. The packing machine divides and packages the food substrate into desired portions for fulfillment and delivery. Accordingly, an extruded food product 34 is produced.

In one embodiment the extruded food product 34 is a pet food such as a dried kibble. In another embodiment the extruded food product 34 is pasta. In yet another embodiment the extruded product 34 is a snack bar. In another embodiment the extruded food product 34 is pasta. In yet another embodiment the extruded product 34 is a cold meat or sausage product.

Importantly, notwithstanding processing of the food substrate, the edible oil having the cannabinoid mixture maintains desired ratios of the acidic cannabinoids or combinations thereof, when compared to the non-acid (decarboxylated forms). Preferably, these ratios are unchanged while the food substrate is infused with the edible oil because the food substrate is maintained at a temperature of less than 80° C.

Figure 2:
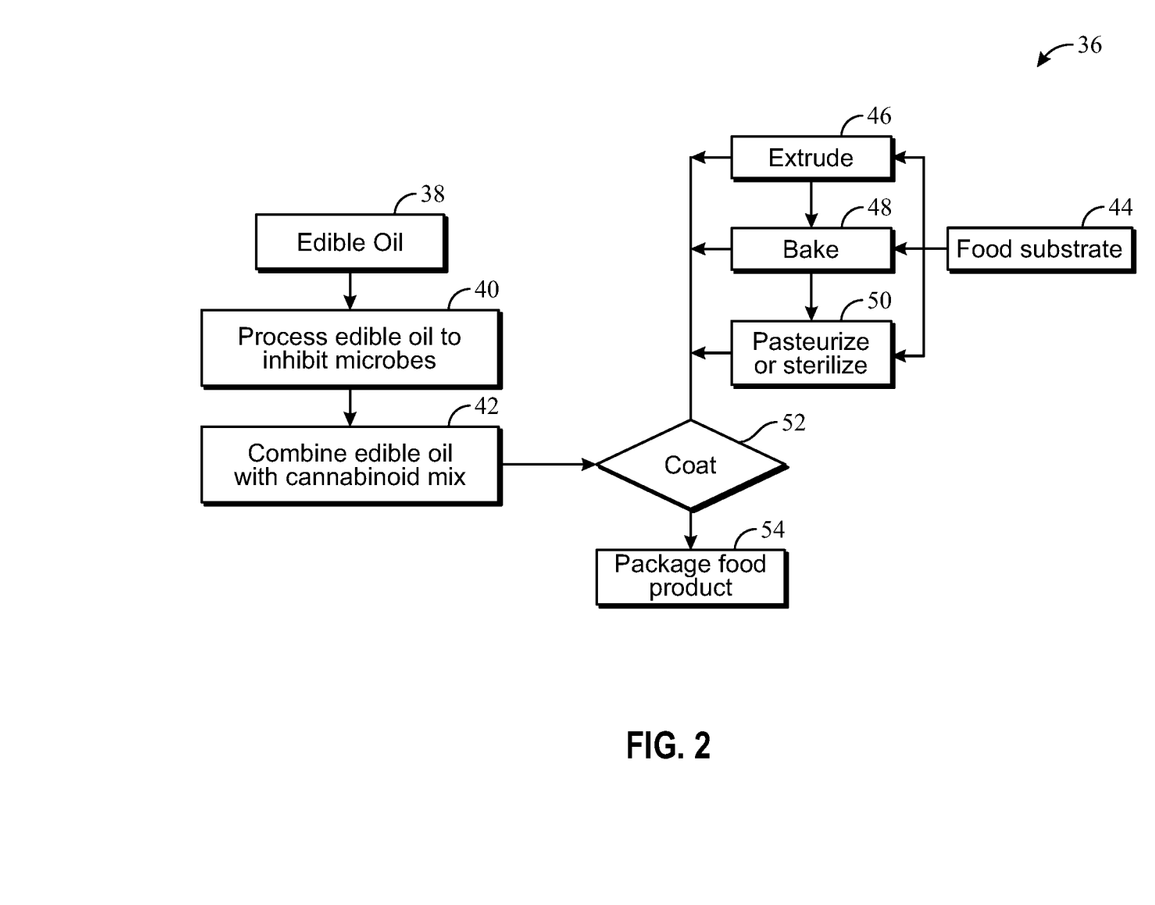
FIG. 2 is method of producing a packaged food product having classical cannabinoids in their acid form.

FIG. 2 shows a flow chart of a method in accordance with the present invention, generally designated with the reference numeral 36. The method 36 includes the step 38 of providing an edible oil, the step 40 of processing the edible oil to inhibit microbes and the step 42 of combining the edible oil with at least one cannabinoid and preferably a mix of cannabinoids. A mix of cannabinoids is termed "cannabinoid mix", which includes at least one cannabinoid such as CBD or THC-A, and other cannabinoids.

The step 40 of processing the edible oil to inhibit microbes can be accomplished by irradiation, heating, pressure treatment or other methods commonly used to treat edible oils. The step of processing increases shelf life and reduces health risks associated with pathogens.

The step 42 combines the processed edible oil with a cannabinoid mixture. In one embodiment the cannabinoids mix is preprocessed to inhibit microbes without significant decarboxylation of cannabinoids contained therein. Ideally no cannabinoids are decarboxylated. In another embodiment the ratio of non-decarboxylated cannabinoids to decarboxylated cannabinoids is at least 9:1.

In yet another embodiment the step of combining 42 precedes the step of processing 40 while maintaining a consistent ratio of non-decarboxylated cannabinoids to decarboxylated cannabinoids. In another embodiment the ratio of non-decarboxylated cannabinoids to decarboxylated cannabinoids is at least 9:1.

The method 36 includes the step 44 of providing a food substrate. The food substrate can be processed in any of a number of ways in order to obtain desired forms. These ways include the step 46 of extruding the food substrate in a hot or cold extrusion process, the step 48 of baking the food substrate, or the step 50 of pasteurizing or sterilizing the food substrate. In addition to these steps, other steps including dehydrating or otherwise cooking the food substrate can be implemented. The steps can be undertaken individually or combined in various ways to achieve food product. After the food substrate is processed, the step 52 coats the food substrate with the edible oil including the cannabinoids mix. The step of coating includes spraying according to one embodiment of the invention. In another embodiment of the invention the food substrate is soaked with the cannabinoid mix. The cannabinoid mix infuses and penetrates the food substrate to create a uniform distribution of cannabinoids in the food substrate. In another embodiment the step of coating 52 includes mixing to assure a uniform concentration of cannabinoids on the food substrate. Coating oils may subsequently penetrate/permeate the food substrate. In another embodiment, the food substrate and edible oil are subjected to a vacuum, wherein the edible oil penetrates and fills voids within the food substrate. The step 54 packages the infused food substrate as a packaged food product.

In one embodiment, the cannabinoid mix includes is hemp oil, such as hemp seed oil, or hemp oil derived from other parts of the hemp plant. The hemp oil is cold-pressed or extracted oil from industrial hemp. Preferably, the hemp oil is processed at 50° C. or lower and applied to the food substrate at 80° C. or lower. In a preferred embodiment of the invention, the hemp oil has no more than 10 ppm (0.001% by dry weight) tetrahydrocannabinol (THC).

In one embodiment the hemp seed is dehulled prior to being cold-pressed to limit psychoactive cannabinoid content, which is concentrated in the hull of the hemp seed.

In another embodiment, the hemp seed is ground prior to being cold-pressed so that cannabinoids in the hull and the endosperm are passed into the hemp oil to increase cannabinoid content of the hemp oil.

While hemp oil is used in various embodiments of the invention, it can be appreciated that the hemp oil can be supplemented by oils derived from other parts of the hemp plant, such as hemp stalk oil, hemp leaf oil, or hemp flower oil. Additionally, fractions derived from hemp oil can be added to the hemp oil. These include cannabinoids, bioactive terpenes, and essential fatty acids. Canine breeds and other mammals are unable to produce some particular essential fatty acids. In one embodiment, the hemp oil includes 60-80% (w/w) linoleic acid and alpha-linoleic acid. More preferably, the hemp oil includes 70-76% (w/w) linoleic acid and alpha-linoleic acid. Other beneficial ratios are possible.

In accordance with the present invention, the cannabinoids and the essential fatty acids of the hemp oil (omega-6 and omega-3 fatty acids) are protected from oxidation in at least one of a number of ways. In one embodiment, an anti-oxidant, or blends of anti-oxidants, are added to the hemp oil. In another embodiment, the hemp oil is blended with another oil to inhibit oxidation.

Preferably, the food product of the present invention includes a maximum oil content of 10% of combined oils by weight. More preferably, the food product of the present invention includes an oil content of with the range of 5% to 10% of combined oils by weight. In another embodiment the oil content is 4-8% of combined oils by weight. In another embodiment the oil content is less than 5% of combined oils by weight.

In one embodiment, the inventive food product includes hemp oil. The hemp oil content of the food product is between 4-8% by weight. In a variation of this embodiment, the hemp oil is blended with a second oil to inhibit oxidation of the acid-form cannabinoids in the hemp oil. The hemp oil includes active cannabinoids in micro-dose concentrations measured in parts per million. Preservation of these cannabinoids it is important to enable the cannabinoids to be bioactive. The blended oil preserves these cannabinoids and inhibits cannabinoid oxidation. The oil content of both the hemp oil and the blended oil remains below 10% of the product by weight.

In another embodiment, the hemp oil is sprayed under vacuum pressure to improve absorption of the oil into the food product and to achieve a desired uniformity of concentration of the hemp oil in the food product. In another embodiment a clay is added to the food product to improve absorption of the oil into the food product. In another embodiment, the hemp oil is applied to the food product at a temperature greater than room temperature and less than the decarboxylation temperature of CBD-A.

Spray coating systems or drum coating systems can be used to apply the oil to the food product. In embodiments where the hemp oil is blended with other oils, animal fat oil can be used, or a vegetable derived oil such as coconut oil, or sunflower oil. Maximum total oil amount is 10%.

Optimally the hemp oil includes 74% (w/w) linolenic acid and alpha-linolenic acid. These fatty acids function as a bioactive excipient that optimally delivers the cannabinoids in vivo.

Essential Fatty Acids.

Linolenic acid (an omega-6 FA) and alpha-linolenic acid (an omega-3 FA) have been measured by investigators as 52-62% and 12-23% (w/w) respectively in hemp oil. In a preferred embodiment the hemp oil is chosen to have approximately 54% omega-6 fatty acids linoleic and gamma linolenic and 18% omega-3 fatty acids alpha linolenic acid and stearidonic acid. This typically yields an approximate 3:1 ratio of omega-6 to omega-3. This ratio nears the 5:1 ratio of omega-6 to omega-3 fatty acids recommended for canine diets is achieved through supplementing with than other plant or meat sourced oils.

Many commercial pet foods in fact contain excess omega-6 which is known to be pro-inflammatory. In addition, hemp oil has phytosterols which can help reduce arterial inflammation. Further, hemp oil is a natural source of several minerals needed for homeostasis, including phosphorous, potassium, magnesium, sulfur, calcium, iron, and zinc. Thus, the present invention balances the ratio of omega-6/omega-3 fatty acids while supplementing phytosterols and minerals such as phosphorous, potassium, magnesium, sulfur, calcium, iron, and zinc. This, in combination with active cannabinoids, functions to reduce inflammation and achieve homeostasis.

The processing methods of the present invention reduce the oxidation of the essential fatty acids as well as the cannabinoids. Thus, the health benefits of the inclusion hemp oil are unencumbered.

Hemp oil samples were tested and contain measurable amounts of CBD and CBD-A, but no measurable THC at a level of quantification (LOQ) of 2.0 ppm. Preferably the CBD-A content averages between 15-35 ppm. In one embodiment, the CBD and CBD-A content of the hemp oil averages between 10-50 ppm, and preferably between 10-40 ppm. Table 2 shows tested samples of hemp oil and indicates various cannabinoid concentrations in parts per million (ppm).

TABLE 2

Unopened samples direct from supplier stored in cool dark place (all values in PPM).

| Lot Number | Organic | THC | Δ8-THC | Δ9-THC | THCA | THCV | CBC | CBD | CBDA | Totals |
|---|---|---|---|---|---|---|---|---|---|---|
| ANBE65NCA | N | 0.00 | 0.00 | 0.00 | 0.00 | 0.00 | 0.00 | 5.10 | 18.80 | 23.90 |
| GEWI15SCA | N | 0.00 | 0.00 | 0.00 | 0.00 | 0.00 | 0.00 | 10.10 | 20.10 | 30.20 |
| DAMA15XCA | N | 0.00 | 0.00 | 0.00 | 0.00 | 0.00 | 0.00 | 10.70 | 26.90 | 37.60 |
| BRSK36NOA | Y | 0.00 | 0.00 | 0.00 | 0.00 | 0.00 | 0.00 | 3.50 | 23.60 | 27.10 |
| ASBA16SOA | Y | 0.00 | 0.00 | 0.00 | 0.00 | 0.00 | 0.00 | 9.90 | 29.70 | 39.60 |
| Avg cannabinoids: | | 0.00 | 0.00 | 0.00 | 0.00 | 0.00 | 0.00 | 7.86 | 23.82 | 31.68 |

Pet Food Ingredients, Methods and Products

Example 1: Canine Feeding Method

The Resting Energy Requirement (RER) for an intact adult dog can be calculated by the formula $RER=1.8*70(BW)^{.35}$ (SACN, p. 61). For a 20-kg dog, this calculation returns a daily caloric requirement of 1162 kcal per day. For a diet containing 3500 kcal/kg, this dog would optimally consume 1162 kcal/day ±3500 kcal/kg=0.332 kg/day, or 332 grains of diet per day. If hemp oil is 2% of the diet, the dog would consume 6.64 grams of hemp oil per day, slightly more than one teaspoonful. One study (Holler, 2008) tested 29 hemp-containing samples of which 7 were oils; the highest concentration of THC found was 7.8 μg/g, or 0.00078%. Using this number, the 20-kg dog in the example above consuming 6.64 grams of oil would receive 0.052 mg of THC, or 0.003 mg/kg/day. Studies in humans, either after single or repeated exposure, identified psychotropic effects as a follow up of a single administration at the same lowest effective dose (the lowest dose tested) of 0.04 mg THC/kg BW, which is deemed to be a realistic approximation of the Lowest Observed Effect Level (LOEL) by the European Food Safety Authority (EFSA, 2011). This proposed use of hemp oil, even if cross-contaminated with THC, is far below the psychotropic LOEL. If greater amounts of hemp oil were anticipated in canine diets, a 20-kg dog fed 332 grains of diet consisting of 5% hemp oil would consume 16.6 grams of oil, or roughly one tablespoonful. Using the scenario above of 7.8 μg/g THC in the oil, this dog would consume 0.13 mg of THC per day, or 0.007 mg THC/kg/day, again well below any psychotropic effect. Accordingly, a method of the present invention includes delivering less than 0.13 mg of THC per day, or 0.007 mg THC/kg/day to a canine subject. Another method of the present invention is providing canine feed to a subject containing 0.02% cold pressed hemp oil, where the feed is manufactured at temperatures which neither oxidize the essential fatty acids in the hemp oil, nor oxidize the bioactive cannabinoids. Optionally, anti-oxidants can be added to the hemp oil to minimize oxidation of fatty acids.

Example 2: Sample Canine Food Formulation

| Ingredient: | % |
|---|---|
| Chicken meal | 0.372 |
| Brown rice | 0.19575 |
| Oats | 0.090 |
| Barley | 0.090 |
| Dried egg | 0.08 |
| Beet pulp | 0.04 |
| Brewers yeast | 0.035 |
| Chicken fat | 0.035 |
| Palatant | 0.035 |
| Hemp oil | 0.02 |
| Salmon Oil | 0.0055 |
| Vitamin/mineral | 0.00175 |
| Total | 1.000 |

Example 3: Sample Canine Food Formulation

| Ingredient: | % |
|---|---|
| Chicken meal | 0.37 |
| Sweet potato | 0.18075 |
| ground peas | 0.12 |
| Chickpeas | 0.12 |
| Dried egg | 0.08 |
| Chicken fat | 0.032 |
| Palatant | 0.035 |
| Brewers yeast | 0.035 |
| Hemp oil | 0.02 |
| Salmon Oil | 0.0055 |
| Vitamin/mineral | 0.00175 |
| Total | 1.000 |

Example 4 Nut Butter (Human Food)

Nut Butters:

Edible oils for human consumption, such as hemp oil including cannabinoids, is mixed with nut butter created by blanching and grinding nuts. The edible oils including cannabinoids have minimal water content and would not normally be acidified so that the cannabinoids do not decarboxylate to a significant degree. In one embodiment, the nut butter is pressure treated before pack-out. In another embodiment, the edible oil is irradiated, filtered and/or pressure treated prior to mixing with the blanched and ground nuts. The cannabinoids have a ratio of acidic to non-acidic forms of the cannabinoids of at least 9:1. In one embodiment, the nut butter contains no detectable THC and only CBD-A. In another embodiment the nut butter contains no detectable THC and a combination of cannabinoids described herein including predominately CBD-A. Preferably, the edible oils and the blanched and dried nuts are simultaneously treated by irradiation, filtering, pressure treatment, or combinations thereof to improve shelf life and to inhibit microbial contamination.

Example 5 Spreads (Human Food)

A spread product includes acidic cannabinoids. Acidic cannabinoids are dissolved in an edible oil, which is mixed at a temperature of less than 80° C. into a spread product. Oils would have minimal water content and would not be acidified so that the acidic cannabinoids do not significantly decarboxylate. Optionally, the product could be pressure treated before pack-out. Optionally, the edible oil is processed to inhibit microbial growth through irradiation, filtering, pressure treatment, or combinations thereof prior to mixing with the spread product. This processing inhibits food-borne illness in consumers and improves shelf life of the spread product.

Example 6 Pourable Dressing (Human Food)

A pourable dressing product includes acidic cannabinoids. Acidic-cannabinoids are dissolved in an edible oil, or presented in the form of hemp oil, which is mixed at a temperature of less than 80° C. into a pourable dressing base. The edible oils have minimal water content and would not be acidified so that the acidic-cannabinoids do not significantly decarboxylate. Optionally, the product could be pressure treated before pack-out. Optionally, the edible oils are processed to inhibit microbial growth through irradiation, filtering, pressure treatment, or combinations thereof prior to mixing with the spread product. This processing inhibits food-borne illness in consumers and improves shelf life of the spread product. Desired combinations of the edible oils and cannabinoids are added, in whole, or in part, to the edible oil in the pourable dressing base.

The pourable dressing has minimal water content and would not be acidified to inhibit decarboxylation of the acidic-cannabinoids. The pourable dressing is pressure treated before pack-out. The edible oil is processed by irradiation, filtering, pressure treatment or combinations thereof prior to addition to the pourable dressing base.

Example 7 Chewing Gum (Human Food)

Edible oils such as hemp oil, that includes a cannabinoid mixture, are added to chewing gum. Optionally, the edible oil could be irradiated, filtered and/or pressure treated prior to addition to the chewing gum.

Example 8 Frozen Dairy Products (Human Food)

Combinations of edible oils and cannabinoids would be added, in whole, or in part, to the oil in the product. Oils would have minimal water content and would not be acidified. Optionally, the product could be pressure treated before pack-out. The oil could be irradiated, filtered and/or pressure treated prior to addition.

Example 9 Confections (Human Food)

A variety of confections can be produced at relatively high temperatures since ordinary sugar has a melting point of about 160° C. Artificial sweeteners, like aspartame (melting point is 248-250° C.), can have higher or lower melting points, which allows for processing at high temperatures. The process of producing confections with or without the heat and pressure combinations in extrusion can alter the cannabinoids and convert acidic forms to non-acidic forms. Cannabinoids can be added with or without other additives, flavorings, or ingredients by contact (drip, spray, bath, etc.) or other forms after the confection is formed or extruded and then cooled to less than 80° C. or lower.

Example 10 Extruded Pet Food

Pet food manufactured by extruding a pet food substrate where an edible oil including cannabinoids is added after drying and while the temperature of the pet food is less than 80° C. Optionally the pet food includes hemp oil as the edible oil. In a further option, the edible oil is infused with extracted or concentrated oil derived from the flowers or leaves of *Cannabis sativa*. Other oils can deliver the same benefits. If not then please delete sections that describe the benefits of hemp oil.

The combination of desired edible oils and the cannabinoids may improve the health of pets including canines, felines and other mammals.

Example 11 Livestock Feed

The present invention includes livestock rations manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 12 Poultry Feed

Feed manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 13 Small Animals

The present invention can be utilized for animals including birds, rodents, fish, herbivorous reptiles and insects. Feeds manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 14 Molded Pet Treats

Injection Molded Foods: target animals include dogs, cats, rodents and birds. Foods manufactured by injection molding where an edible oil including cannabinoids is added to the mix prior to molding and while maintaining the processing temperature at less than 80° C. Alternatively, an edible oil including cannabinoids is applied/coated onto molded products. In a further example, the molded product may be a treat rather than nutritionally complete food.

Example 15 Sausage (Human Food)

Dry Cured Sausage: a variety of sausages can be made by adding salt and nitrite/nitrate to meats and drying the mixtures at refrigeration temperatures. After sufficient moisture is removed then the mixtures can be further dehydrated at warmer temperatures. An edible oil including cannabinoids is added to the mix prior to drying. Optionally the meat mixtures can be smoked during dehydration. Optionally, an edible oil including cannabinoids is applied/coated onto sausages.

Although this invention pertains primarily to integration of cannabinoids into processed food products without significant molecular modification, the products and processes of the present invention can utilize any combination of cannabinoids, including combinations of the following cannabinoids: A-9-tetrahydrocannibolic acid (THC-A), A-9-tetrahydrocannibolic acid (THC-B), A-9-tetrahydrocannibolic acid-$C_4$ A and/or B (THC-A-$C_4$), A-9-tetrahydrocannibivarinic acid (THCVA), A-9-tetrahydrocannibiorcolic acid A and/or B (THC-A-$C_1$), A-8-tetrahydrocannibolic acid ($A^8$-THC-A), cannabicyclolic acid (CBL-A), cannabidiolic acid (CBD-A), cannabigerolic acid (CBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabielsoic C3 acid B (CBEA-$C_3$ B) and cannabinolic acid (CBNA).

While the present invention is described in terms of various embodiments of the invention and examples thereof, the scope of the present invention is defined in the appended claims. Further it can be appreciated that the concentrations of edible oils, particularly hemp oil, can be utilized in all of the mentioned food products. Also, the micro-dosing, preservation, and concentration of cannabinoids including cannabidiolic acid can be utilized in all of the mentioned food products as well as other food products. The present invention can be used for a variety of pet foods including feline, canine, and others. Further, the present invention can be used for livestock feed, as well as for human food.

What is claimed is:

1. A pet food product, comprising:
    a food substrate;
    hemp oil having cannabidiolic acid (CBD-A) concentration of between 15-35 ppm, and tetrahydrocannabinol (THC);
    the ratio of CBD-A to THC is at least 1.88:1;
    second oil blended with the hemp oil to inhibit oxidiation of the CBD-A; and
    the blended combination of hemp oil and the second oil are applied to the food substrate and do not exceed 5% of the food product by weight.

2. A pet food product, comprising:
    A food substrate;
    Hemp oil having a cannabidiol (CBD) concentration of between 15-35 ppm, and tetrahydrocannabinol (THC);
    the ratio of CBD to THC is at least 1:3;
    a second oil being blended with the hemp oil to inhibit oxidation of the CBD; and
    the blended combination of hemp oil and the second oil are applied to the food substrate and do not exceed 10% of the pet food product by weight.

3. A pet food product, comprising:
    a food substrate;
    hemp oil having a cannabidiolic acid (CBDA), and tetrahydrocannabinol (THC) in a concentration of less than 100 ppm in the hemp oil;
    the ratio of CBDA to THC is at least 1:3;
    a second oil being blended with the hemp oil to inhibit oxidation of the CBDA and the THC; and
    the blended combination of hemp oil and the second oil are applied to the food substrate and do not exceed 10% of the pet food product by weight.

* * * * *